United States Patent [19]

Shorter et al.

[11] Patent Number: 4,463,459
[45] Date of Patent: Aug. 7, 1984

[54] ENDO-SKELETAL ARTIFICIAL LIMB

[75] Inventors: John J. Shorter; Victor J. Woolnough; Michael W. Brewer, all of Hampshire, England

[73] Assignee: Chas. A Blatchford & Sons Limited, Hampshire, England

[21] Appl. No.: 303,843

[22] Filed: Sep. 21, 1981

[30] Foreign Application Priority Data

Sep. 25, 1980 [GB] United Kingdom ................. 8031039

[51] Int. Cl.³ ............................................... A61F 1/08
[52] U.S. Cl. ................................................ 3/30; 3/4; 403/141; 403/143
[58] Field of Search ............... 3/30, 31; 403/131, 141, 403/143

[56] References Cited

U.S. PATENT DOCUMENTS

| 1,811,736 | 6/1931 | Van Bezel | 403/143 |
| 2,296,469 | 9/1942 | Kastler | 403/143 X |
| 2,422,302 | 6/1947 | Horn | 403/143 X |
| 3,424,419 | 1/1969 | Siegel | 403/143 X |
| 3,874,050 | 4/1975 | White | 29/149.5 B |
| 4,306,320 | 12/1981 | Delp | 3/31 |

FOREIGN PATENT DOCUMENTS 1211354 8/1960 Fed. Rep. of Germany ............ 3/31

Primary Examiner—Richard J. Apley
Assistant Examiner—David Isabella
Attorney, Agent, or Firm—Barnes & Thornburg

[57] ABSTRACT

An artificial leg has a ball and socket ankle joint, the socket of which has upper and lower portions. They are connected together and clamped over the ball by a turnbuckle ring. This provides an adjustable shin and foot connection which permits use of a rubber-encased ball of sufficient size, without taking up too much shape within the ankle region. Also disclosed is a movable patella member and a vertically jointed two part foam covering.

4 Claims, 8 Drawing Figures

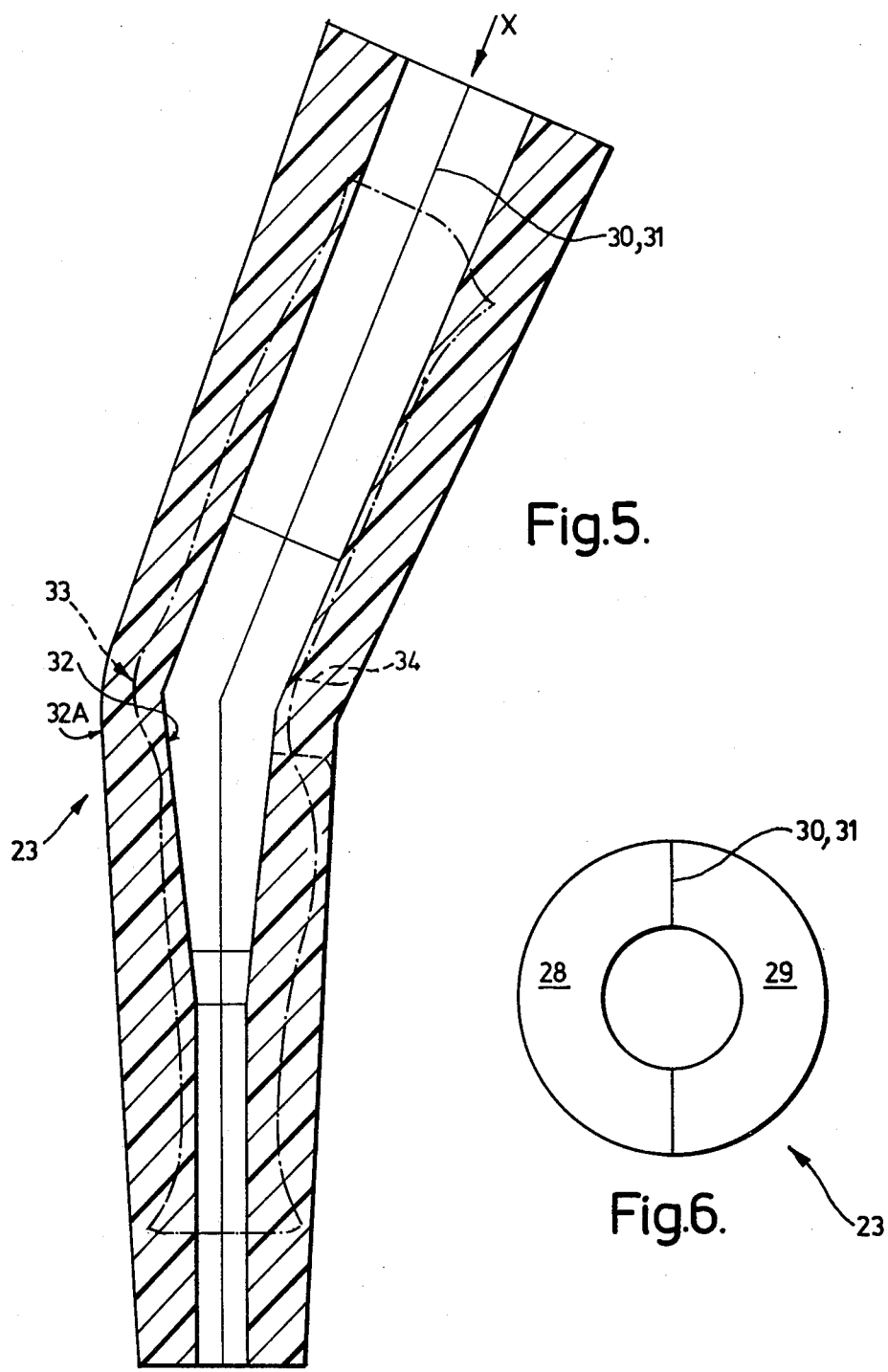

ENDO-SKELETAL ARTIFICIAL LIMB

FIELD OF THE INVENTION

This invention relates to an artificial limb and more particularly although not exclusively to an endo-skeletal artificial leg. An endo-skeletal leg is one in which internal structural members, such as a thigh socket or socket container and a shin tube member, are enclosed in an outer covering, which may for example be of plastics foam.

DESCRIPTION OF THE PRIOR ART

It is known for an endo-skeletal artificial leg to have a separate foot which is connected to a shin member by means of a ball and socket ankle joint. The ball and socket type of ankle joint permits appropriate flexion of the shin relative to the foot. It is known to provide a generally spherical rubber cover over the ball and within the socket, to lessen transmission shock from the foot up into the shin. But for such an arrangement to be effective the amount of rubber present in the rubber cover must be sufficient, so that the ball must be of sufficient size to provide for the required minimum amount of rubber: this in turn requires the ball-enclosing socket to be of an appreciable size. It is desirable to provide means whereby the foot is readily removable and replaceable, and also it is desirable that the position or angle of the foot be readily adjustable relative to the shin. A problem arises in satisfying these desirable requirements of, on the one hand, a ball and socket ankle joint of appreciable size and, on the other hand, means associated with the ankle joint for adjusting the foot relative to the shin, because of the restricted amount of space available within the ankle zone of the foot and shin. It is one object of this invention to provide an artificial leg which overcomes this problem.

It is also known to provide an endo-skeletal artificial limb with various types of outer, non-structural covering. For example, it is known to provide such a covering in the form of a continuous tubular sleeve of flexible foam material fitted over the thigh portion, the knee portion, and the shin of an artificial leg. The advantages of such a sleeve are that it is light in weight and can be made to give the leg a relatively acceptable appearance compared for example with an artificial leg in which a cosmetic covering has a gap at the knee. However the main disadvantage of the known continuous foam sleeve is its susceptibility to wear and deterioration in the knee region due to repeated flexing of the knee joint, which causes alternate tensioning and compression of the foam material. The plastics foam materials which are most suitable for a cosmetic sleeve are generally much weaker when subjected to tensile stress than when compressed. It is therefore the stretching of the foam material over the internal structural members which tends to cause deterioration of the sleeve.

The design of such a limb covering sleeve tends to be a compromise governed by the conflicting requirements of of providing a sleeve which is sufficiently flexible such that movement of the knee joint is not impeded and at the same time is sufficiently durable. It must also maintain an appearance which approximately matches that of a natural limb in both the flexed and extended positions of the knee joint.

It is another object of this invention to provide an artificial leg in which these requirements are satisfied to a greater extent than previously.

It is a further object of this invention to provide means which reduces the amount of deformation which a plastics foam covering sleeve must undergo in the knee region when the leg is flexed at the knee.

SUMMARY OF THE INVENTION

According to one feature of this invention, there is provided an artificial leg having a shin member, a foot, and a ball and socket joint connecting the shin member and foot, characterized in that the socket has upper and lower socket portions which fit around the ball, the upper socket portion being connected to the shin member and the two socket portions being connected together by, and clamped around the ball by, a rotatable sleeve-like member which, on rotation in one direction, causes the two socket portions to move towards each other to clamp the ball.

According to another feature of this invention there is provided a jointed endo-skeletal artificial limb having a tubular plastics foam covering, characterized in that the covering is formed of at least twoelongate cover portions whose mating surfaces extend in the generally longitudinal direction of the limb, the shape of at least one of the elongate cover portions, before formation of the covering, being such that the completed tubular covering is subjected predominantly to compressive rather than tensile forces over its normal range of flexion.

According to a further feature of this invention there is provided a jointed endo-skeletal artificial limb having a foam covering disposed over the joint and having a structural member in the region of the joint, characterized by the provision of a movable member which is connected to the structural member in the region of the joint, the movable member being disposed in such manner that it determines the external shape of that part of the foam covering which projects outwardly from the joint when the artificial limb is in its flexed position.

The invention also includes a method of manufacturing a tubular plastics foam covering or sleeve for an endo-skeletal jointed artificial limb, characterized in that the method comprises: moulding one of two elongate cover portions to a shape matching the shape of the limb when in its extended position; moulding the other of the two elongate cover portions to a shape matching the shape of the limb when in as flexed position; bonding the two moulded portions together along longitudinal mating surfaces to form the completed tubular covering, whereby the completed tubular covering is subjected predominantly to compressive stress rather than tensile stress when the artificial limb is moved between flexed and extended positions.

An artificial leg in accordance with the invention preferably has a relatively lightweight carbon fibre shin which connects a knee joint to an ankle joint. The shin may have an intermediate attachment point for a swing control device or a simple knee lock mechanism. In horizontal cross section the shin is U-shaped in its upper region and of closed, preferably circular, cross section in its lower region. The limb may have a foot and ankle assembly which is similar to the known SACH (solid-ankle cushioned-heel) foot construction, but which has the cushioned ball-and-socket ankle joint mentioned above. This joint may have a light alloy ball mounted on a light alloy peg which is adjustably fixed in the foot.

The ball may have a bonded rubber covering. The socket member mounted at the lower end of the shin member is in two parts which are clamped together by for example a turnbuckle ring. The turnbuckle ring is rotatable about the shin axis and has a right-hand thread portion which engages one part of the socket member and a left-hand thread portion which engages the other part of the socket member. When the ring is rotated the two parts are drawn together in a direction parallel to the shin axis to clamp the ball. The provision of this ankle joint gives a degree of cushioning to lessen the transmission of shock from the foot to the leg. It also allows the foot to be aligned relative to the shin by loosening the turnbuckle ring, adjusting the position of the foot, and retightening the ring. This adjustment allows the foot to be positioned beneficially relative to other parts of the leg, notaly the thigh socket, to provide good static and dynamic alignment to suit individual patient requirements. The foot may be otherwise similar to known SACH foot types with a soft foam section on the heel, a solid central keel attached to the ankle joint and a balata belt anterior extension.

In a preferred embodiment, the plastics foam covering for an artificial leg may comprise an anterior cover section and a posterior cover section. These two sections are individually moulded so that, prior to being bonded together, the anterior section is shaped to correspond approximately to the flexed leg and the posterior section is shaped to correspond approximately to the leg in its extended position. When the two sections are brought together, the anterior section is subject to compression especially in the region covering the knee. When the covering is fitted to the limb, and the limb is in its extended position the anterior section is compressed and the posterior section is in a relaxed state. When the knee joint is flexed the compression is transferred to the posterior section and the anterior section moves towards its natural unstressed position.

Therefore this covering has the advantage over known foam coverings that it is not subjected to damaging tensile stress over a substantial range of movement of the leg, so reducing the rate of deterioration of the foam material.

As referred to above, a jointed endo-skeletal artificial limb with a foam covering disposed over the joint has a movable outer member which is attached to a structural member of the limb in the region of the joint. In an artificial leg this outer member may be a patella member which moves towards the knee joint axis as that joint is flexed. This has the effect of reducing the extent to which the foam covering on the anterior side of the joint has to be deformed as the joint is moved to and fro between the fully extended and fully flexed positions. In the preferred embodiment the patella member is generally semi-circular when viewed in the medial/lateral direction and is pivotally attached to the shin. The rounded surface of the member is in contact with the inner surface of the foam covering and creates a projecting area which simulates the front of the natural knee. As the knee joint is flexed the patella member slides over a cam surface of reducing radius relative to the joint axis so that the patella member effectively retracts, so reducing the deformation of the covering. The patella member also acts as a kneeling member. Alternatively, the patella member may be linked to a point in the thigh above the knee axis. A further feature of the preferred embodiment is the provision of a recess or cut-out in that part of the covering which lies in the angle of the limb when the joint is flexed. Such a reduction in the amount of foam material in this region minimises the possibility of "bunching" of the foam covering which, apart from being unsightly, may prevent full flexion of the knee joint or may cause premature failure failure of the covering.

BRIEF DESCRIPTION OF THE DRAWINGS

The invention will now be described by way of example, with reference to the drawings, in which:

FIG. 5 is an enlarged section of the whole covering, with the two portions of FIGS. 3 and 4 bonded together;

FIG. 6 is a top plan view as seen in the direction of the arrow "X" in FIG. 5;

DESCRIPTION OF THE PREFERRED EMBODIMENT

Figure 1:
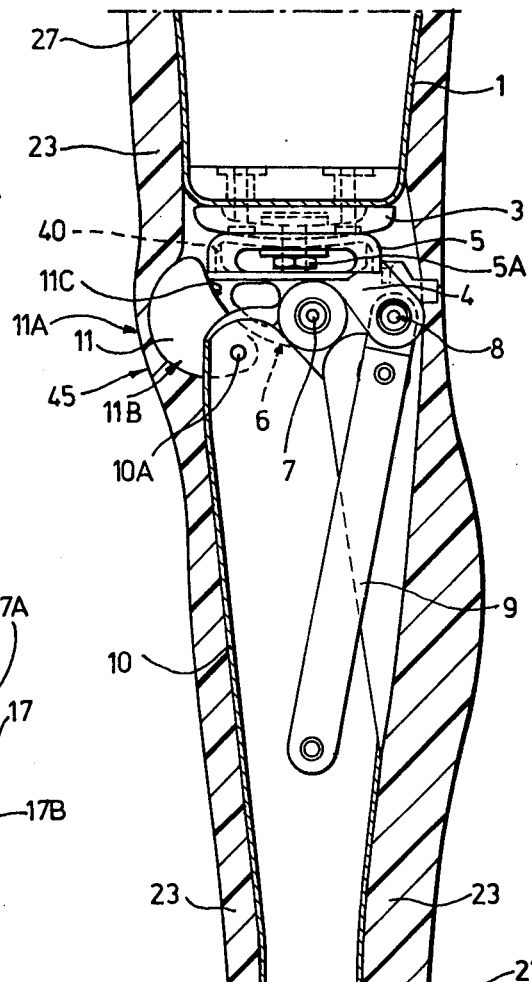
FIG. 1 is a vertical central section of an artificial leg in accordance with the invention, with the thigh portion cut away at its upper end.
Figure 2:
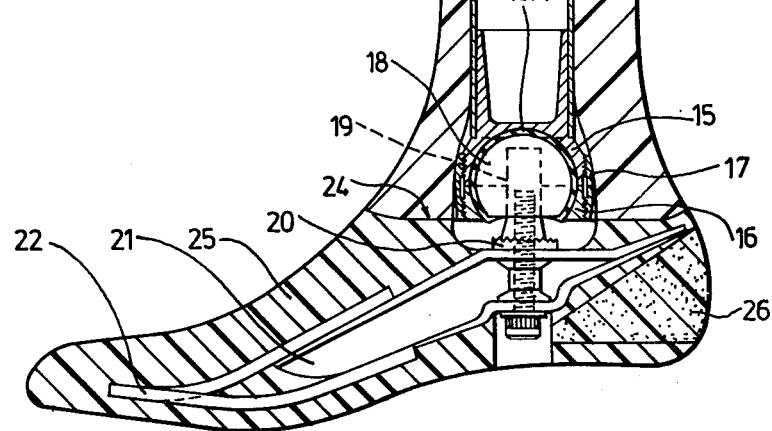
FIG. 2 is an enlarged detail section of part of the ankle joint.

Referring to FIG. 1 an endo-skeletal artificial leg has a plurality of main internal structural components comprising:

a polypropylene thigh socket container 1, the top part of which is cut away and not shown;

a convex alignment plate 3 bolted to the base of the socket container 1;

a knee chassis 4 with a concave spherical cup 5 which interfaces with the alignment plate 3; the knee chassis 4 is attached to the alignment plate 3 by a central clamp bolt 5A; the chassis 4 has a curved cam surface 6 of decreasing radius relative to the knee joint axis 7, and a rear pivotal attachment 8 for a knee lock device, which is indicated diagrammatically at 9;

a carbon fibre shin member 10 which is movable angularly about the knee joint axis 7 from the extended position shown in FIG. 1;

the shin member 10 has a pivotal attachment point 10A for a movable patella member 11 which slides over the cam surface 6 as the shin member 10 moves about the knee axis 7;

an ankle assembly comprising a ball and a socket joint which connects the shin member 10 to a foot, the socket having upper and lower socket portions 15, 16 which fit around a ball 18, the upper socket portion 15 being connected to the shin member 10 and the two socket portions 15, 16 being connected together by, and clamped around the ball 18 by, a rotatable sleeve-like turnbuckle ring member 17, which, on rotation in one direction, causes the two socket portions 15, 16 to move towards each other to clamp the ball 18. Between the ball 18 and socket portions 15, 16 is a rubber lining 18A. (The relatively large size of the ball and socket joint in the ankle region will be noted).The ball 18 is mounted on a peg 19 having aserrated lower surface 20; and a foot keel 21 in the form of a carbon fibre box section which is adjustably mounted on the peg 19; the keel 21 has a forward extension 22.

The several structural members of the leg are surrounded by a continuous flexible foam covering or sleeve 23, described below with reference to FIGS. 3 to 6. The covering 23 extends from the socket container 1, over the knee joint and the shin, and is bonded to the upper surface 24 of the foot. The foot is also of endoskeletal construction and has a body 25 of relatively stiff foam enclosing the keel 21. A part 26 of relatively soft foam is provided in the heel. The whole leg has an outer flexible cover 27 of a silicone sheet material.

Figure 3:
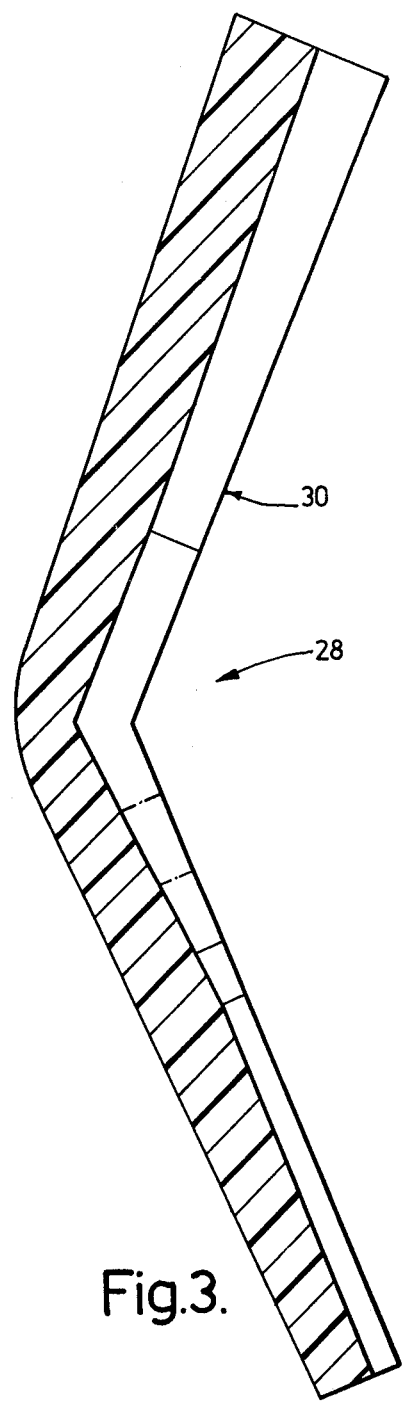
FIG. 3 is an enlarged section of a front or anterior covering portion.
Figure 4:
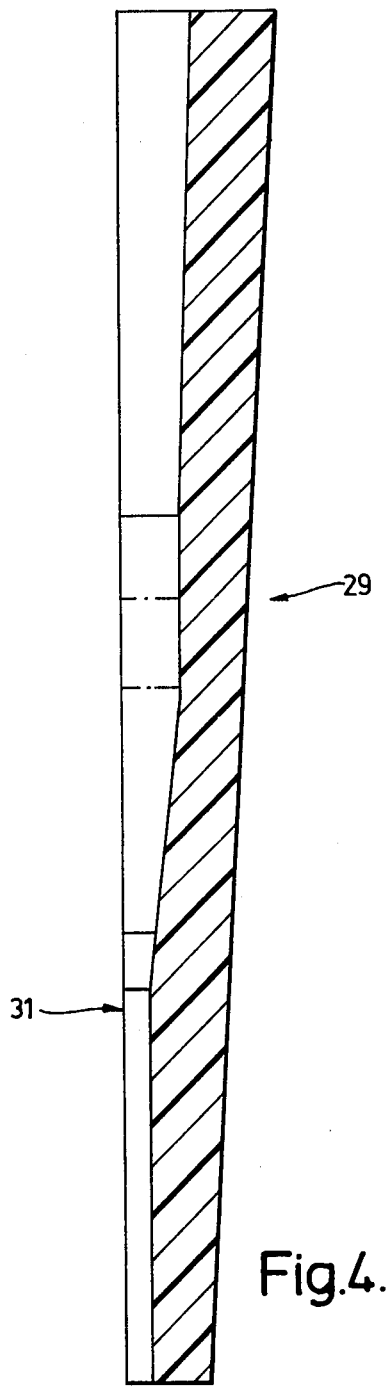
FIG. 4 is an enlarged section of a rear or posterior covering portion.

Referring to FIGS. 3 and 4, the cosmetic covering 23 is formed from two cover sections 28, 29 which are individually moulded in the shapes shown. The anterior section 28 (FIG. 3) is moulded such that in its unstressed condition it corresponds approximately to the shape of the leg in a partly flexed portion. Conversely the posterior section 29 (FIG. 4) is moulded without the angle of the section 28, i.e. its shape corresponds to the leg in its extended position.

To produce the complete covering 23 shown in FIG. 5, the two sections 28 and 29 are bonded together along the longitudinally extending surfaces 30 and 31 (see also FIG. 6), with the result that the section 28 is compressed in the region of the knee.

The inner moulded surface 32 of the covering 23 corresponds to the shape of the structural components of the limb. The outer surface 32A is a temporary surface and is trimmed down by for example linishing to produce the required final exterior surface 33 indicated by dotted lines in FIG. 5. The ends of the covering 23 are then trimmed to length as also indicated by dotted lines and some foam material is removed from the region behind the knee by forming a cut-out 34 as shown.

The covering 23 is then ready to be fitted over the structural components as shown in FIG. 1.

Figure 7:
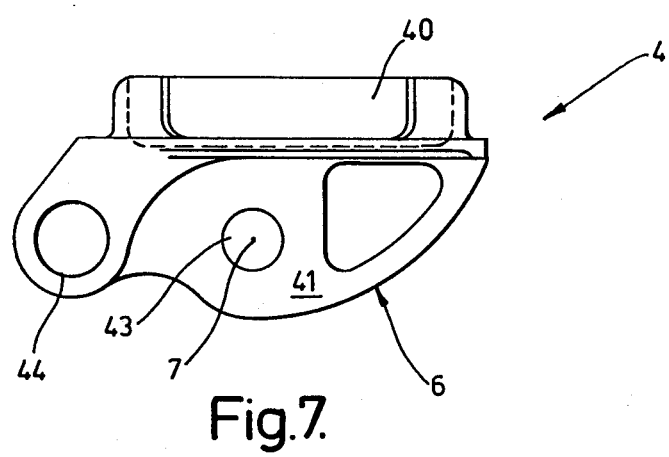
FIG. 7 is an enlarged side elevation of a knee chassis.
Figure 8:
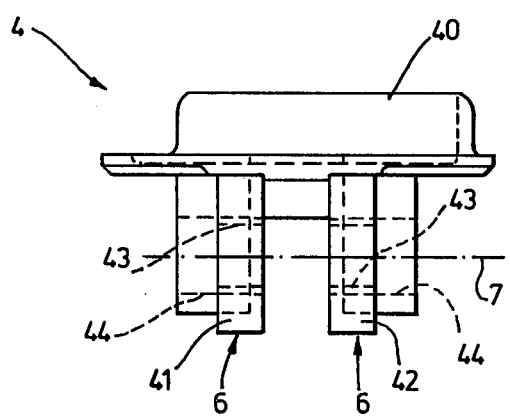
FIG. 8 is a front elevation of the knee chassis of FIG. 7.

Referring now to FIGS 1, 7 and 8, the knee chassis 4 and movable patella member 11 will now be described. The knee chassis 4 has an upwardly extending rim 40 which fits within the cup 5 of the alignment coupling. The chassis has two depending portions 41, 42 each formed with the lower curved cam surface 6 referred to above. These portions 41, 42 also have aligned bores 43 for pivotal connection at the knee joint axis 7 of the shin member 10 (see FIG. 1). The depending portions 41, 42 also have aligned bores 44 for the pivotal attachment 8 of the knee lock device 9. As is seen in FIG. 1, a generally semicircular patella member 11 is pivotally mounted at 10A at the upper end of the shin member 10. It has a convex curved front surface 11B and a concave curved rear surface 11C, the latter being in sliding engagement with the camming surfaces 6. The front surface 11B is in contact (as seen in FIG. 1) with the inner surface of the plastics foam covering 23 and creates a projecting area 45 which simulates the appearance of a natural knee. As the leg is flexed about the knee joint axis 7, the patella member 11 slides over the cam surfaces 6 which are of reducing radius relative to the axis 7 so that the patella member 11 becomes retracted, moving rearwardly about its pivotal attachment point 10A, and so reducing the deformation of the covering 23. Thus as the leg is flexed about the knee joint axis, the motion of the patella member causes the extent of the resultant deformation of the plastics foam covering 23 in the anterior knee region to be reduced.

We claim:

1. An artificial leg comprising a shin member, a foot, and a joint therebetween comprising a ball having a rubber covering, fixed to the foot, and a socket enveloping the ball and covering, the socket having upper and lower socket portions which fit around the ball and covering, the upper socket portion being connected to the shin member, a rotatable sleeve-like member surrounding the socket and wherein said rotatable sleeve-like member having spaced, oppositely threaded inner surface portions to engage correspondingly threaded outer surface portions of said upper and lower socket portions, respectively, the upper and lower socket portions being connected together and clamped around the ball and covering by the rotatable sleeve-like member such that rotation in one direction of the rotatable sleeve-like member causes the two socket portions to move towards each other to clamp the ball and covering.

2. An artificial leg according to claim 1 further comprising a peg projecting upwardly from the foot, the ball being mounted on an upper end of the peg.

3. An artificial leg according to claim 2 wherein the peg further comprises means for adjustably connecting the peg to the foot so as to permit adjustable movement of the foot with respect to the peg in a horizontal direction relative to the vertical orientation of the shin member.

4. An artificial leg according to claim 1 wherein the rubber covering is bonded to the ball.

* * * * *